United States Patent [19]

Hemel et al.

[11] Patent Number: 5,046,853
[45] Date of Patent: Sep. 10, 1991

[54] MEASURING THE DEGREE OF DISPERSION IN FLOWING SUSPENSIONS

[75] Inventors: Ralf Hemel, Lampertheim; Friedrich Linhart, Heidelberg, both of Fed. Rep. of Germany

[73] Assignee: BASF Aktiengesellschaft, Ludwigshafen, Fed. Rep. of Germany

[21] Appl. No.: 365,131

[22] Filed: Jun. 12, 1989

[30] Foreign Application Priority Data

Jun. 21, 1988 [DE] Fed. Rep. of Germany ....... 3820902

[51] Int. Cl.⁵ ...................... G01N 15/06; G01N 21/05
[52] U.S. Cl. .................................................. 356/440
[58] Field of Search ................... 356/72, 73, 336, 338, 356/440, 442; 73/863.01, 863.03, 863.83, 864.21

[56] References Cited

U.S. PATENT DOCUMENTS

| | | | |
|---|---|---|---|
| 3,661,460 | 5/1972 | Elking et al. | 356/442 |
| 4,683,212 | 7/1987 | Uffenheimer | 356/73 |
| 4,752,131 | 6/1988 | Eisenlauer et al. | 356/338 |
| 4,761,074 | 8/1988 | Kohsaka et al. | 356/338 |

Primary Examiner—Richard A. Rosenberger
Attorney, Agent, or Firm—Keil & Weinkauf

[57] ABSTRACT

A flow cell through which the sample stream is passed surrounded by an enveloping stream is equipped with a laser-optical measuring means. For use in pressurized systems the inlet of the cell for the enveloping stream medium is connected on the upstream side to a constant pressure and flow means and the outlet from the cell is connected on the downstream side to a regulating means for the sample and enveloping stream flow rate.

1 Claim, 1 Drawing Sheet

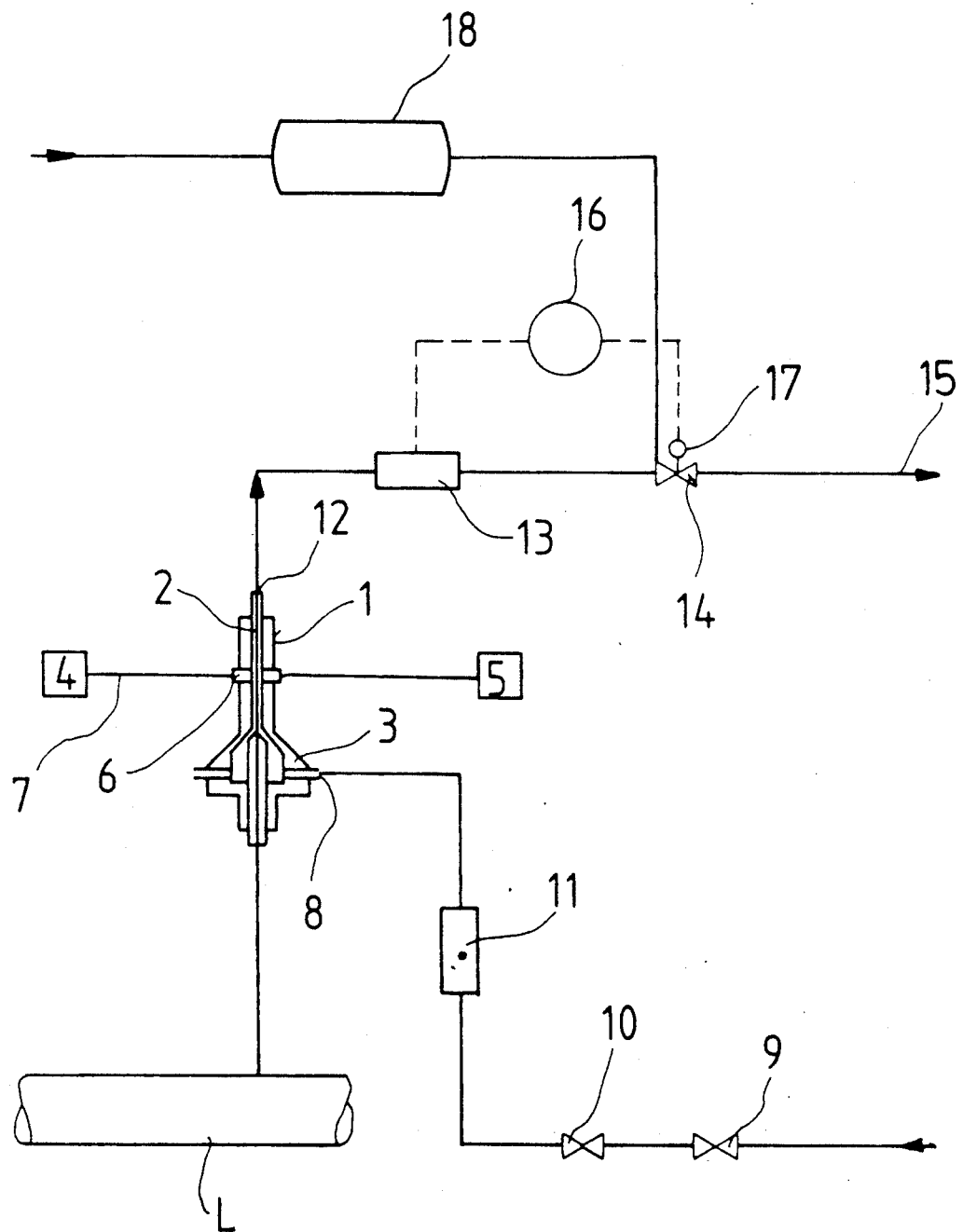

MEASURING THE DEGREE OF DISPERSION IN FLOWING SUSPENSIONS

The present invention relates to an arrangement for measuring the degree of dispersion in flowing suspensions.

Rapid in situ measurement of the degree of dispersion in flowing systems is possible with a laseroptical method not only in laboratory tests for assessing the effectiveness of dispersants or flocculants but also in the on-line inspection and regulation or control of dispersing and flocculating units, for example in paper machines. The laser-optical method involves the detection and analysis of fluctuating scattered light, shading or reflectance signals from flowing particles and/or particle ensembles. A hardware realization of this method is described in DE-A-3,412,620. There the measurement takes place in a flow cell not on a particle ensemble as with a simple turbidity measurement but on individual particles. This can be effected either by focusing the laser light to a beam diameter of the order of magnitude of the particles to be measured or by individualizing the particles in a capillary flow.

The known apparatus is not easily usable with pressurized systems. Furthermore, its high unreliability owing to blockages prevents the use in practical systems. Pressure fluctuations in the system likewise have an adverse effect.

It is an object of the present invention to implement the abovementioned laser-optical method in a hardware form for reliable use in pressurized systems.

We have found that this object is achieved by an arrangement for measuring the degree of dispersion in flowing suspensions, comprising a sample stream flow cell which is constructed as an enveloping stream cell and is equipped with a laser-optical measuring means, a constant pressure and flow means upstream of the inlet for the enveloping stream, and a regulating means downstream of the outlet from the cell for the sample and enveloping stream flow rate. The drawing schematically shows the overall measuring arrangement according to the invention, including the constant pressure and flow means provided upstream of the inlet for the enveloping stream, and the regulating means provided downstream of the outlet from the flow cell for the sample and enveloping stream flow rate.

In what follows, the measuring arrangement according to the invention is described with reference to an illustrative embodiment schematically depicted in the drawing.

The central part of the measuring arrangement is a flow cell 1 where the sample stream 2, taken from a suspension line L, is separated by an enveloping stream 3 from a transmitter 4 and a receiver 5 and on the transmitter side there is a means 6 for ensuring that the laser light bundle from a single light guide fiber 7 is parallel or focused and has a diameter of the order of magnitude of the flowing particles.

The laser-optical measuring means 4-7 connected to the cell causes the flowing particles to give off scattered light, shading or reflectance signals which are recorded by a photodetector via an appropriate imaging system as voltage-current fluctuations with time which, by a subsequent effective value measurement, are correlated with the degree of dispersion of the flowing system. Further details of the cell and of the measuring means are described in DE-A-3,412,620.

The enveloping stream, which keeps the optical windows of the cell clear from deposits, must be kept constant. This is achieved by placing upstream of the inlet 8 of the cell 1 for the enveloping stream medium, for example water, a constant pressure and flow means. It consists of the in-series connection of a pressure reducing valve 9, a constant pressure valve 10 and a flow rate meter 11. Flow rate means 11 as provided on the inlet side of the enveloping stream medium keeps the flow rate constant by internal means so that no external regulating means for this flow rate meter are required.

The total sample and enveloping stream in the cell is flow rate controlled. To this end, the outlet 12 from the cell 1 is likewise connected to a flow rate meter 13 which is connected via a pinch valve 14 to an outflow 15. A PI or PID regulator 16 is driven by the measured signal from the flow rate meter, the signal output regulator being connected to an adjusting member 17 for the valve 14. It is advisable to connect a damping vessel 18 upstream of the pneumatic inlet of the adjusting member to prevent free oscillation of the system on account of the short control loop.

We claim:

1. An arrangement for measuring the degree of dispersion in flowing suspensions, comprising a sample stream flow cell which is constructed as an enveloping stream cell and is equipped with a laser-optical measuring means, a constant pressure and flow means upstream of the inlet for the enveloping stream, and a regulating means downstream of the outlet from the cell for the sample and enveloping stream flow rate, the regulating means for the sample and enveloping stream consisting of a flow rate meter, a regulator driven thereby and a pinch valve connected via an adjusting member to the output of the regulator.

* * * * *